United States Patent
Pai et al.

(10) Patent No.: US 7,674,767 B2
(45) Date of Patent: Mar. 9, 2010

(54) NANOPARTICLE COMPOSITIONS OF WATER-SOLUBLE DRUGS FOR ORAL ADMINISTRATION AND PREPARATION METHODS THEREOF

(75) Inventors: Chaul Min Pai, Daejeon (KR); Mi Hong Min, Daejeon (KR); Jun Seok Hwang, Daejeon (KR); Kyung Mi Cho, Seoul (KR)

(73) Assignee: Samyang Corporation, Seoul (KR)

( * ) Notice: Subject to any disclaimer, the term of this patent is extended or adjusted under 35 U.S.C. 154(b) by 131 days.

(21) Appl. No.: 10/584,449

(22) PCT Filed: Dec. 24, 2004

(86) PCT No.: PCT/KR2004/003448

§ 371 (c)(1),
(2), (4) Date: Jun. 22, 2006

(87) PCT Pub. No.: WO2005/061004

PCT Pub. Date: Jul. 7, 2005

(65) Prior Publication Data

US 2007/0154559 A1 Jul. 5, 2007

(30) Foreign Application Priority Data

Dec. 24, 2003 (KR) .................. 10-2003-0096641

(51) Int. Cl.
*A61K 38/28* (2006.01)
*A61K 47/06* (2006.01)
*C09D 105/04* (2006.01)

(52) U.S. Cl. .................. 514/3; 530/303; 106/31.33; 424/1.33

(58) Field of Classification Search .................. None
See application file for complete search history.

(56) References Cited

U.S. PATENT DOCUMENTS

| 5,510,118 | A | 4/1996 | Bosch et al. |
| 2003/0054027 | A1* | 3/2003 | Unger .................. 424/450 |
| 2003/0095928 | A1 | 5/2003 | McGurk et al. |
| 2005/0170004 | A1* | 8/2005 | Rosenberger et al. ....... 424/490 |

FOREIGN PATENT DOCUMENTS

| EP | 0771566 | * | 7/1997 |
| WO | WO-2004/043513 | * | 5/2004 |

OTHER PUBLICATIONS

Sakuma, et al., 2001, Advanced drug delivery review, 47, 21-37.*
Sakuma et al., "Design of nanoparticles of graft copolymers for oral peptide delivery", Advanced Drug Delivery Reviews, vol. 47, pp. 21-37, (2001).
Leroux et al., "Pharmacokinetics of a Novel HIV-1 Protease Inhibitor Incorporated into Biodegradable or Enteric Nanoparticles following Intravenous and Oral Administration to Mice", J. Pharm. Sci., vol. 84, No. 12, pp. 1387-1391, (Dec. 1995).

* cited by examiner

*Primary Examiner*—Andrew D Kosar
*Assistant Examiner*—Satyanarayana R Gudibande
(74) *Attorney, Agent, or Firm*—Birch, Stewart, Kolasch & Birch, LLP

(57) ABSTRACT

The present invention relates to an orally administrable composition containing nanoparticles with the particle size of 500 nm or less, comprising 0.1-30 weight % of a complex of a water-soluble drug and a counter-ion substance in which the charged water-soluble drug is bonded with the counter-ion substance, 0.5-80 weight % of a lipid, 0.5-80 weight % of a polymer, and 1-80 weight % of an emulsifier, wherein the weight ratio of said lipid and said polymer is in the range of 1:0.05-3, and a preparation method thereof. The composition of the present invention has high gastrointestinal absorption rate upon oral administration, and has high drug entrapping rate in the nanoparticle, and is also stable against lipases.

17 Claims, 4 Drawing Sheets

NANOPARTICLE COMPOSITIONS OF WATER-SOLUBLE DRUGS FOR ORAL ADMINISTRATION AND PREPARATION METHODS THEREOF

CROSS-REFERENCE TO RELATED APPLICATIONS

The present application is the U.S. National Phase entry of PCT/KR2004/003448, for which priority is claimed under 35 U.S.C. §120. This application also claims priority under 35 U.S.C. §119(a) of Patent Application No. 10-2003-0096641 filed in Korea on Dec. 24, 2003.

BACKGROUND OF THE INVENTION (1) Field of the Invention

The present invention relates to orally administrable nanoparticle compositions comprising water-soluble drugs with enhanced gastrointestinal absorption rate, and preparation methods thereof. Specifically, the present invention relates to orally administrable nanoparticle compositions having enhanced entrapping rate of water-soluble drugs within nanoparticles composed of lipids and polymers, and being stable against lipases, wherein the nanoparticles are prepared by binding water-soluble drugs with counter-ion substances and adding lipids, polymers, and emulsifiers thereto, and preparation methods thereof.

(2) Description of Related Art

Water-soluble drugs including physiological active agents, protein drugs, have low stability in the gastrointestinal tract and low permeability to the wall of intestinal tract, and thus intravenous injection has been usually used for the drugs. However, intravenous injection is not convenient for most patients in daily lives, and so there have been many efforts to prepare water-soluble drugs into orally administrable formulations.

In case water-soluble drugs are orally administered, the drugs are chemically degraded by action of pH and digestive enzymes whose stability is decreased in the gastrointestinal tract. Thus, most or some parts of the administered drugs could not play their role, and so desired pharmacological effects could not be adequately expressed upon oral administration. Particularly, when the drugs have the decreased solubility or are degraded as pH changes, they loose their potency by the action of gastrointestinal enzymes and show extremely low bioavailability. To solve such problems, there have been studies to prepare formulations for water-soluble drugs, wherein the drugs are not exposed to external chemical environments, e.g. pH or digestive enzymes, by entrapping them within lipids or polymers with high affinity with biological membranes.

For example, orally administrable formulations for water-soluble drugs using W/o or w/o/w emulsion, or liposome are known in the art. However, they have drawbacks of having insufficient drug entrapping rate and low stability.

U.S. Pat. No. 6,004,534 discloses targeting such water-soluble drugs as vaccines or allergens to specific tissues by using targeted liposome therefor. However, it has the problem of having low drug entrapping rate of about 35% in the liposome.

U.S. Pat. No. 6,191,105 discloses preparation of w/o micro-emulsion formulations of insulin polymers. However, the structures of w/o emulsions may be usually disrupted by phase transition upon administration into the body, and thus, drugs dissolved in aqueous phase cannot be protected by oily phase, and are directly exposed to the body.

U.S. Pat. No. 6,277,413 discloses preparation of w/o/w emulsions wherein water-soluble drugs are introduced into the internal aqueous phase. However, in this patent, the particle size of the prepared emulsion is extremely large, 10 to 20 micrometers, and during its preparation, the drugs entrapped in the internal aqueous phase are likely to be released to the external aqueous phase, and thus, the emulsion has low drug entrapping rate.

Korean Patent Laid-open No. 2002-66776 discloses orally administrable formulations of insulin by using monoglyceride lipid carrier of 500 nM or less. However, the carrier consists of only lipid, and thus, may be degraded by lipases in vivo.

Journal of Controlled Release 69, p283-295 (2000) discloses PLGA microspheres containing insulin with less than 50% of drug entrapping rate and more than 5 micrometers of particle size. It has been reported that 100 nanometer-sized particles are absorbed into the intestinal tract 15 to 250 times more than micrometer-sized particles whereas micrometer-sized particles cannot be absorbed into the intestinal tract, and are generally found in the surface of epithelial cells in the intestine [Pharm. Res. 13 (12) p 1838-1845 (1996)]. Therefore, 5 μm-sized PLGA microspheres have only low insulin entrapping rate and deliver insulin less effectively than nanometer-sized particles.

Further, U.S. Pat. No. 5,962,024 discloses dissolving drugs at pH 6.5 or higher by preparing granules or coating the granules with enteric polymers, e.g. hydroxypropyl methylcellulose acetate succinate or methacrylic methyl methacrylate copolymer. However, microspheres formed only from enteric polymers have the drawback that it cannot stabilize drugs unstable in the gastrointestinal tract because the polymers are dissolved in the intestinal tract and the drugs entrapped in the microspheres are exposed in the intestinal tract.

On the other hand, only low fractions of water-soluble drugs are entrapped in carriers composed of lipophilic substances or polymers due to their low affinity with said carriers, and thus, their water-solubility should be lowered by eliminating their charges to enhance drug entrapping rate in the carriers.

WO 94/08599 discloses preparation of complexes wherein insulin is ionically bonded with sodium lauryl sulfate. This preparation method is to dissolve insulin-sodium lauryl sulfate complexes in an organic solvent and use the solution as pulmonary or suppository formulations. However, upon oral administration, the drug is directly exposed to the gastrointestinal tract, and so cannot be maintained stable.

Further, U.S. Pat. No. 5,858,410 discloses nano-particulating water-insoluble drugs by milling and using a microfluidizer, but this has the drawback that this is not suitable for water-soluble drugs unstable in vivo, e.g. protein drugs, because the drugs are directly exposed to in vivo environment.

As described above, for oral administration of water-soluble drugs unstable in vivo including protein drugs, nanoparticles stable against lipases in the gastrointestinal tract should be designed and water-soluble drugs should be entrapped in drug carriers with high efficiency. Technical requirements to achieve these purposes are as follows.

First, to maintain drugs entrapped in nanoparticles stable with no degradation in the gastrointestinal tract, lipid nanoparticles should contain appropriate amounts of polymers to increase their stability in vivo.

Second, entrapping rates of water-soluble drugs in lipophilic carriers should be increased by preparing water-soluble drugs into complexes with counter-ion substances and selecting lipid/polymer systems with the similar affinity thereto to have affinity with lipophilic carriers by modifying water-soluble drugs Third, particle sizes of lipid/polymer nanoparticles containing complexes of water-soluble drugs and counter-ion materials should be minimized. Also, nanoparticles should be prepared so that the drugs are entrapped within the nanoparticles, and so are not exposed to external environment and are absorbed into the body with maintaining their maximal activity.

BRIEF SUMMARY OF THE INVENTION

The present inventors have repeated extensive studies to solve the above-described problems and to develop drug carriers satisfying the above technical requirements. As a result, the present inventors discovered that drug entrapping rate and resistance against degradation enzymes in vivo can be increased by preparing orally administrable nanoparticle compositions with the particle size of 500 nm or less from water-soluble drug-counter-ion substance complexes and a certain ratio of a lipid and a polymer, etc., and completed the present invention.

The purpose of the present invention is to provide orally administrable nanoparticle compositions with enhanced drug entrapping rate and resistance against lipases by containing complexes of water-soluble drugs and counter-ion substances thereby having increased oral absorbability in vivo, and preparation method thereof.

DETAILED DESCRIPTION OF THE INVENTION

Figure 1:
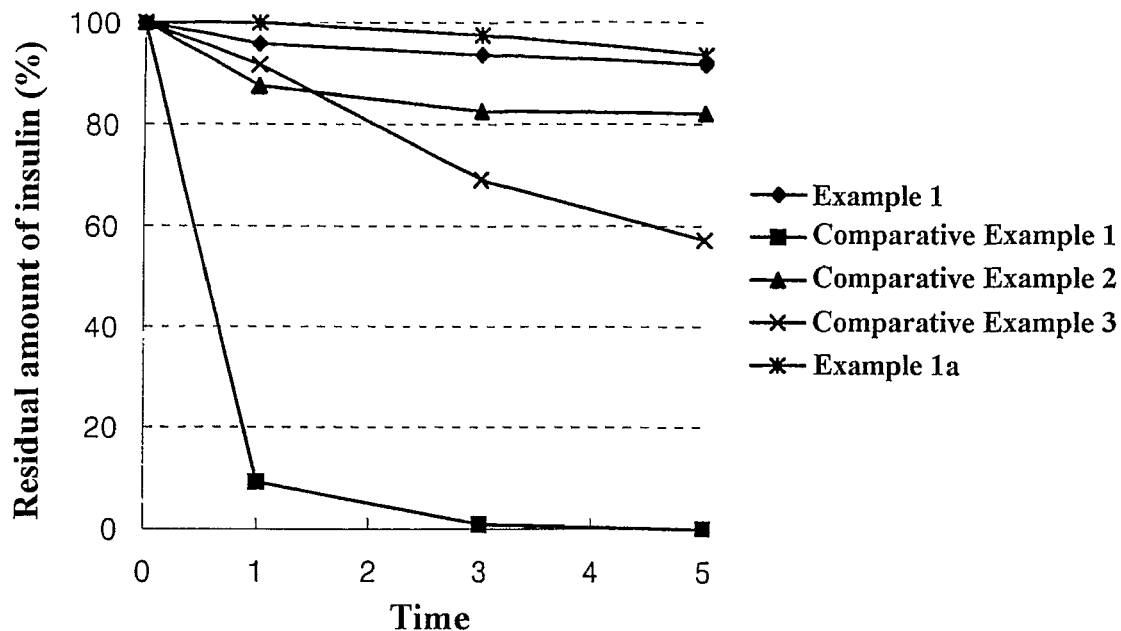
FIG. 1 is a graph showing stability of the orally administrable nanoparticle composition of the present invention containing insulin as an active ingredient against pancreatin (protease/lipase) in Experiment 2.
- ◆ -: Example 1
- ■ -: Comparative Example 1
- ▲ -: Comparative Example 2
- X -: Comparative Example 3
- * -: Example 1a FIG. 2 is a graph showing the relative blood glucose concentration after intra-intestinally administering the oral nanoparticle composition of the present invention containing insulin as an active ingredient to type 1 diabetic rats in Experiment 3(2).
- ◆ -: Reference group (insulin-containing buffer of pH 7.4, dosage of insulin 3 IU/kg)
- ■ -: Example 1 (dosage of insulin 3 IU/kg)

The present invention provides an orally administrable composition containing nanoparticles with the particle size of 500 nm or less, which comprises 0.1 to 30 weight % of a complex of a water-soluble drug and a counter-ion substance in which the charged water-soluble drug is bonded with the counter-ion substance, 0.5 to 80 weight % of a lipid, 0.5-80 weight % of a polymer, and 1 to 80 weight % of an emulsifier, wherein the weight ratio of said lipid and said polymer is in the range of 1:0.05-3. The weight ratio of said lipid and said polymer is preferably in the range of 1:0.2-1.

Further, the present invention provides a method for preparing the orally administrable nanoparticle composition according to the present invention, comprising the steps of: (a) ionically bonding a charged water-soluble drug with a counter-ion substance to form a complex of the water-soluble drug and the counter-ion substance; (b) adding a lipid, a polymer, and a solubilizing agent to the obtained complex and dissolving the whole mixture, and then, introducing the obtained solution to an aqueous solution containing an emulsifier to obtain a homogeneous liquid phase; (c) eliminating the solubilizing agent from the mixture obtained in step (b); and (d) optionally, minimizing the particle size using a microfluidizer.

According to the present invention, the water-soluble drug is entrapped in the nanoparticle composition at the rate of 70% or more, and can be retained at the rate of 80% or more in the presence of pancreatin enzymatic solution.

Still further, the present invention provides a method for preparing the orally administrable nanoparticle composition according to the present invention, comprising the steps of:

(a) ionically bonding a charged water-soluble drug with a counter-ion substance to form a complex of the water-soluble drug and the counter-ion substance; (b) adding a lipid and a solubilizing agent to the obtained complex and dissolving the whole mixture, and then, introducing the obtained solution to an aqueous solution containing an emulsifier and a polymer to obtain a homogeneous liquid phase; (c) eliminating the solubilizing agent from the mixture obtained in step (b); and (d) optionally, minimizing the particle size using a microfluidizer.

Hereinafter, the present invention will be explained in detail.

The orally administrable nanoparticle composition of the present invention comprises 0.1 to 30 weight % of a complex of a water-soluble drug and a counter-ion substance wherein the charged water-soluble drug is ionically bonded with the counter-ion substance, 0.5 to 80 weight % of a lipid, 0.5 to 80 weight % of a polymer, and 1 to 80 weight % of an emulsifier, wherein the weight ratio of said lipid and said polymer is in the range of 1:0.05-3, and comprises nanoparticles with the particle size of 500 nm or less. The weight ratio of said lipid and said polymer is preferably in the range of 1:0.2-1.

The complex of the water-soluble drug and the counter-ion substance is obtained by reaction of the charged drug with the counter-ion substance. The water-soluble drug used as an active ingredient may be ones charged in an aqueous solution, preferably, ones charged in water selected from the group consisting of peptide/protein drugs such as insulin, erythropoietin, calcitonin, growth hormone, interferon, somatostatin and the like, heparin, cepha antibiotic, sodium alendronate, sodium etidronate, sodium pamidronate, etc.

A negatively charged substance which can be ionically bonded to a positively charged drug may be preferably selected from the group consisting of sodium salt of $C_{8-18}$ fatty acid such as sodium docusate, sodium oleate, sodium lauryl sulfate, sodium caproate, sodium laurate, etc., sodium salt of bile acid, sodium alginate, and sodium carboxymethylcellulose. A positively charged substance which can be ionically bonded with a negatively charged drug may be preferably selected from a quaternary ammonium compound such as carnitine salt, benzalkonium chloride, cetrimide, etc.

The content of the complex of the water-soluble drug and the counter-ion substance is preferably 0.1 to 30 weight % of the total weight of the nanoparticle composition.

When a water-soluble drug forms a complex with a counter-ion substance, the original charge of the water-soluble drug is removed or weakened, thereby to increase its affinity with lipophilic carrier. As a result, the water-soluble drug can be entrapped more in the lipophilic carrier. As shown in the following Table 4 in Experiment 1, the composition of the present invention shows high drug entrapping rate.

The molar ratio of the water-soluble drug and the counter-ion substance in the complex of the water-soluble drug and the counter-ion substance may be adjusted depending on the number of ions of the water-soluble drug, preferably to 1:0.1-20, more preferably to 1:3-10.

Said lipid may be preferably one or more selected from an aliphatic alcohol such as monoglyceride, diglyceride, propylene glycol ester of fatty acid (Capriol, etc.), glycerol ester of fatty acid (GELucier, etc.), cetostearyl alcohol, cetyl alcohol, etc., and may be preferably contained at 0.5 to 80 weight %, more preferably 0.5 to 30 weight %, of the total weight of the nanoparticle composition.

Said polymer may be preferably one or more selected from an enteric polymer such as methacrylic acid copolymer, hydroxypropyl methylcellulose phthalate, hydroxypropyl methylcellulose acetate succinate, cellulose acetate phthalate, etc., shellac, chitosan, hydroxypropyl methylcellulose and its derivative, ethylcellulose, methylcellulose, polyvinyl alcohols, sodium alginate, and carbomer, and may be preferably contained at 0.5 to 80 weight %, more preferably 0.5 to 30 weight %, based on the total weight of the nanoparticle composition. Particularly, in case of using an enteric polymer, drugs labile in gastric acid, e.g. proteins, are not disrupted and can be readily absorbed into small or large intestine selectively depending on composition of the enteric polymer.

Said polymer is insoluble in water or becomes viscous when dissolved in water, and so is slowly degraded when added to a lipid nanoparticle, thereby controlling dissolution rate of a water-soluble drug entrapped in the nanoparticle. Also, said polymer surrounds surface of the lipid nanoparticle and is inserted between the lipid molecules, and thus, imparts enzyme resistance to the nanoparticle. That is, addition of polymer can prevent degradation of the lipid, a structural component of the nanoparticle, by action of lipases, and thus, the structure of the nanoparticle can be maintained, and the chemical stability of the water-soluble drug entrapped in the nanoparticle can be remarkably improved.

In adding polymer to the lipid nanoparticle composition, the size of the lipid nanoparticle can be varied depending on content of the polymer, and the ratio of lipid and polymer should be appropriately adjusted to obtain the nanoparticle of 500 nm or less.

Said emulsifier is preferably one or more selected from polyoxyethylene polyoxypropylene copolymer (commercial name: Poloxamer™), polyethylene glycol alkyl ether (commercial name: Brij™), polyoxyethylene castor oil (commercial name: Tween™), polyoxyethylene sorbitan fatty acid ester (commercial name: Span™), transesterification product of natural vegetable oil triglyceride and polyalkylene polyol (commercial name: Labrafil™, Labrasol™), glycerol fatty acid ester (commercial name: Plurol™ oleique), vitamin E polyethyleneglycol succinate (Vitamin E polyethylene glycol succinate), lecithin, sodium lauryl sulfate, and bile acid and derivatives thereof, and may be preferably contained at 1 to 80 weight % based on the total weight of the nanoparticle composition. More preferably, the emulsifier may be contained at 30 to 80 weight %. When the prepared lipid/polymer nanoparticles are dispersed in an aqueous solution, the emulsifier stabilizes the dispersion.

Said solubilizing agent may be preferably one or more selected from $C_{1-8}$ alcohol, dimethylsulfoxide, dichloromethane, toluene, propyleneglycol, polyethyleneglycol, and 12-hydroxystearate (commercial name: Solutol™). The solubilizing agent is eliminated while preparing the nanoparticles, and thus, is preferably present in the final nanoparticle composition at 50 weight % or less. In addition, if the solubilizing agent alone cannot dissolve or disperse the complex of a water-soluble drug and a counter-ion substance, a polymer, a lipid, etc., the above described emulsifier may be added thereto to obtain a homogeneous solution.

Further, the composition may contain a conventionally used oral absorbability enhancing agent at 0 to 20 weight %, and said oral absorbability enhancing agent may be preferably selected from p-glycoprotein inhibitor, carnitine salt, chelating agent, etc.

Also, the present composition may be preferably lyophilized with 0.1-30 weight % of a cryoprotective agent, and so be prepared to powder, and then to conventional oral dosage forms such as capsules or tablets. The cryoprotective agent may be preferably a saccharide such as glucose, mannitol, sorbitol, trehalose, an amino acid such as arginine, a protein such as albumin, etc.

The orally administrable nanoparticle composition of the present invention is prepared by the process comprising the steps of: (a) ionically bonding a charged water-soluble drug with a counter-ion substance to form a complex of the water-soluble drug and the counter-ion substance; (b) adding a lipid, a polymer and a solubilizing agent thereto to dissolve the whole mixture, and then, adding the obtained solution to an aqueous solution containing an emulsifier to obtain a homogeneous liquid phase; (c) eliminating the solubilizing agent from the mixture obtained in step b); and (d) optionally, minimizing the particle size using a microfluidizer.

In the above step (a), the complex of the water-soluble drug and the counter-ion substance is prepared by dissolving the drug in water or a suitable buffer to obtain an aqueous solution containing the drug, and then, reacting the counter-ion substance with the drug solution.

The optimal ratio of the water-soluble drug and the counter-ion substance is adjusted considering the number of ions of the drug within the range of the molar ratio of 1:0.1-20, and determined by analyzing the non reacted drug in the above reaction. Preferably, the obtained complex of the water-soluble drug and the counter-ion substance is washed with water three times or more to eliminate the non reacted drug.

Particularly, in preparing a complex of a protein drug and a counter-ion substance, a pH adjusting agent may be used to confer charges on the protein drug. The pH adjusting agent may be selected from an acidifying agent such as hydrochloric acid, phosphoric acid, carbonic acid, citric acid, etc., an alkalifying agent such as sodium hydroxide, sodium/potassium monohydrogen phosphate, sodium/potassium dihydrogen phosphate, sodium phosphate, sodium citrate, etc., or a buffer consisting of their mixtures, and may be used at 0.1 to 10 fold amount of the drug.

In the above steps (b)-(c), the complex of the water-soluble drug and the counter-ion substance, and a lipid are dissolved in a solubilizing agent, and then, the solution is introduced into an aqueous solution containing a polymer, the mixture is stirred, and then, the solubilizing agent is eliminated therefrom. In this step, to increase solubility of the polymer, an acid, an alkali, and an emulsifying aid may be added thereto at 0.5-50 weight %, and the mixture may be heated, preferably to 30-70° C.

In the above step (c), if the solubilizing agent is highly volatile, it may be eliminated by injecting nitrogen gas or using vacuum evaporator. If not, it may be eliminated by dialysis.

In the above step (d), the solution is preferably cyclized 3 to 10 times at 100 MPa using a microfluidizer. If desired, the particle size of the nanoparticle may be further reduced by heating. The heating temperature is preferably 30-70° C.

Another method of preparing the orally administrable composition of the present invention is one comprising the steps of: (a) ionically bonding a charged water-soluble drug with a counter-ion substance to form a complex of the water-soluble drug and the counter-ion substance; (b) adding a lipid and a solubilizing agent thereto to dissolve the whole mixture, and then, adding the obtained solution to an aqueous solution containing a polymer and an emulsifier to obtain a homogeneous liquid phase; (c) eliminating the solubilizing agent from the mixture obtained in step (b); and (d) optionally, minimizing the particle size using a microfluidizer.

The obtained nanoparticle composition is liquid, and if desired, may be lyophilized with a cryoprotective agent to be obtained as powder. Said cryoprotective agent is used for preventing denaturation of ingredients in the composition during lyophilization. The cryoprotective agent may be preferably used at 0.1-30 weight % based on the total weight of the nanoparticle composition. The cryoprotective agent may be preferably a saccharide such as lactose, mannitol, trehalose, etc., an amino acid such as arginine, a protein such as albumin, etc.

The liquid and powder composition obtained as described above may be readily dispersed into water by simple physical mixing, e.g. by shaking with hand, and the particle size forming the dispersion system is 500 nm or less depending on properties of used emulsifier or drug, which is much smaller than prior orally administrable formulations. Preferably, the particle size of the present orally administrable nanoparticle composition is 20-300 nm.

The nanoparticle powder composition of the present invention can be stored stable for a long period of time by sealing at room temperature or lower, and can be prepared into a dispersion solution by adding water thereto prior to use.

Further, the nanoparticle composition of the present invention can be formulated into solution, suspension, capsules, tablets, etc. by adding other absorption enhancing agents, and in solid formulations, its oral bioavailability can be further increased via conventional formulating techniques, e.g. enteric coating, etc.

Hereinafter, the present invention will be described in more detail with reference to the following examples, but the scope of the present invention should not be construed to be limited thereby in any manner.

EXAMPLES

Example 1

Preparation of an Orally Administrable Nanoparticle Composition Containing Insulin (1) Preparation of a Complex of Insulin and a Counter-Ion Substance 50 mg of Insulin (Sigma) was dissolved in 20 ml of citrate buffer of pH 3, and sodium docusate (Aldrich) dissolved in 80 ml of pH 3 citrate buffer was reacted therewith at the molar ratios of 1:3, 1:6 and 1:9 to 1 mole of insulin, to obtain a complex of insulin and the counter-ion substance. Upon completing the reaction, insulin in the supernatant was analyzed according the insulin analysis method described in the US Pharmacopoeia, to obtain results as shown in the following Table 1.

TABLE 1

Reaction ratio of the complex of insulin and the counter-ion substance

| Molar ratio of insulin:sodium docusate | Residual reactant in supernatant |
|---|---|
| 1:3 | 20.7% |
| 1:6 | 0% |
| 1:9 | 0% |

As shown in the above Table 1, most of the insulin formed the complex with the counter-ion substance when the molar ratio of insulin and sodium docusate was 1:6 or more. Therefore, the complex prepared from insulin and the counter-ion substance at the molar ratio of 1:6 was washed with each of citrate buffer of pH 3 and water three times, and then, used for the subsequent step.

(2) Preparation of an Orally Administrable Nanoparticle Composition Containing Insulin 15 mg of Insulin-sodium docusate complex and 60 mg of mono-olein (TCI) were dissolved in 10 ml of ethanol. The solution was introduced into 20 ml of an aqueous solution containing 20 mg of chitosan (Korea Chitosan) and 200 mg of Poloxamer 407™ (BASF), and the whole mixture was stirred to obtain a homogenous solution, and then, ethanol was eliminated therefrom by injecting nitrogen gas thereto. 1% of citric acid was added thereto as an additive to increase the solubility of chitosan. The lipid/polymer nanoparticle was cyclized ten times at 100 MPa of room temperature using a microfluidizer, EmulsiFlex-C5™ (Avestin), to obtain the orally administrable nanoparticle composition containing insulin.

(3) Measurement of Particle Size and Distribution

The particle size and degree of dispersion of the composition were measured according to photon spectrometry (ELS-8000™, Otsuka electronics) after 200 µl of the obtained liquid composition was dispersed into 1 ml of distilled water. As a result, the mean particle size of the liquid composition of Example 1 was 83.0 nm and the degree of dispersion thereof was 0.300.

Comparative Example 1

The liquid composition was prepared according to the same method as Example 1, except using insulin instead of the insulin-counter-ion substance complex and using neither polymer nor microfluidizer. The particle size and degree of dispersion were measured according to the method of Example 1, and as a result, the mean particle size was 117.4 nm and the degree of dispersion was 0.251.

Comparative Example 2

The liquid composition was prepared according to the same method as Example 1, except using insulin instead of the insulin-counter-ion substance complex and not using the microfluidizer. The particle size and degree of dispersion were measured according to the method of Example 1, and as a result, the mean particle size was 241.8 nm and the degree of dispersion was 0.090.

Comparative Example 3

15 mg of the insulin-counter-ion substance complex obtained according to the method of Example 1 and 60 mg of mono-olein were sonicated at 50° C. for 1 hour, and then, were introduced into 20 ml of 1% citrate aqueous solution containing 20 mg of chitosan and 200 mg of Poloxamer 407™, and sonicated once again for 30 minutes. Then, the mixture was cyclized ten times at 100 MPa and at room temperature using a microfluidizer, to obtain a liquid composition containing the insulin complex. As a result of measuring the particle size and degree of dispersion according to the method of Example 1, the mean particle size was 211.6 nm, and the degree of dispersion was 0.213.

Example 1a

The liquid composition was prepared according to the same method as Example 1 except that the microfluidizer was not used. As a result of measuring the particle size and degree of dispersion according to the method of Example 1, the mean particle size was 234.3 nm, and the degree of dispersion was 0.291.

Example 2

Preparation of an Orally Administrable Nanoparticle Powder Formulation Containing Insulin In solidifying the orally administrable nanoparticle liquid formulation obtained from Example 1, increase of the nanoparticle size was minimized by adding 5% of mannitol to the orally administrable nanoparticle liquid formulation, and then, the liquid formulation was solidified under different lyophilization conditions, and dispersed in water to measure the particle size. The results are shown in the following Table 2.

TABLE 2

| | Lyophilizing condition | Before lyophilizing (nm) | After lyophilizing (nm) | Increasing rate of particle size before and after lyophilizing |
|---|---|---|---|---|
| Condition I | Room temperature, 48 hrs | 68.1 | 339.8 | 5.0 |
| Condition II | 0° C.: 12 hrs → 0° C.: 8 hrs → 5° C.: 24 hrs | 82.5 | 188.5 | 2.3 |
| Condition III | −25° C.: 24 hrs → 0 ° C.: 24 hrs | 118.1 | 196.4 | 1.7 |

As shown in the above Table 2, lyophilizing under the condition of <0° C. is preferable for minimizing the variation in the particle size.

To the orally administrable nanoparticle liquid formulation, mannitol was added at 0.5%, 1%, 2%, 4% and 5%, and then, the mixture was solidified at −25° C. for 6 hours, and subsequently, 20° C. for 6 hours. The obtained solid was dispersed into water, and then, the particle size was measured according to the method of Example 1. The results are shown in the following Table 3.

TABLE 3

| | −25° C., 6 hrs → 20° C., 6 hrs | |
|---|---|---|
| mannitol | Particle size | Increasing rate of the particle size before and after lyophilizing |
| 0.5% | 394.1 nm | 3.4 |
| 1% | 335.1 nm | 2.8 |
| 2% | 321.6 nm | 2.7 |
| 4% | 217.3 nm | 1.8 |
| 5% | 196.4 nm | 1.7 |

As a result of the measurement, the variation in the particle size could be minimized when the concentration of the cryoprotective agent was about 5%.

Example 3

Preparation 2 of an Orally Administrable Nanoparticle Formulation Containing Insulin In Example 1, sodium lauryl sulfate (Sigma) was used at the ratio of 1:7 instead of sodium docusate to obtain a complex of insulin and the counter-ion substance. The complex of insulin and the counter-ion substance, mono-olein, and polyethyleneglycol 2000 were weighed 15 mg, 45 mg, and 90 mg, respectively, and were dissolved in 10 ml of ethanol. According to the same procedure, the orally administrable nanoparticle composition containing insulin was prepared.

According to the method of Example 1, the particle size and degree of dispersion were measured, and as a result, the mean particle size was 121 nm, and the degree of dispersion was 0.314.

Example 4

Preparation 3 of an Orally Administrable Nanoparticle Composition Containing Insulin The orally administrable nanoparticle composition containing insulin was prepared according to the same method as Example 1 except using Labrafac™ (Gattefosse) instead of mono-olein. According to the method of Example 1, the particle size and degree of dispersion were measured, and as a result, the mean particle size was 129.4 nm, and the degree of dispersion was 0.227.

Example 5

Preparation 4 of an Orally Administrable Nanoparticle Composition Containing Insulin The orally administrable nanoparticle composition containing insulin was prepared according to the same method as Example 1 except using 60 mg of 1:1 mixture of Eudragit™ (Rohm) and Eudragit S™ (Rohm) instead of chitosan. According to the method of Example 1, the particle size and degree of dispersion were measured, and as a result, the mean particle size was 194.2 nm, and the degree of dispersion was 0.128.

Comparative Example 4

The liquid formulation was prepared according to the same method as Example 5 except using neither mono-olein nor microfluidizer. According to the method of Example 1, the particle size and degree of dispersion were measured, and as a result, the mean particle size was 350.9 nm, and the degree of dispersion was 0.009.

Example 6

Preparation of an Orally Administrable Nanoparticle Containing Ceftriaxone (1) Preparation of a Complex of Ceftriaxone and a Counter-Ion Substance 100 mg of Ceftriaxone (Hawon fine chemical) was dissolved in 20 ml of distilled water, and benzalkonium chloride (Sigma) was weighed in the molar ratio of 1:2 to ceftriaxone and dissolved in distilled water, and then, the reaction was performed at 4° C. The supernatant was taken and ceftriaxone was analyzed according to the ceftriaxone analysis method in the US Pharmacopoeia. As a result, it was confirmed that 99.9% of ceftriaxone formed the complex with the counter-ion substance.

(2) Preparation of an Oral Liquid Formulation Containing Ceftriaxone 120 mg of the complex of ceftriaxone and the counter-ion substance, 60 mg of mono-olein, and 30 mg of 1:1 mixture of Eudragit L™ and Eudragit S™ were dissolved in 15 ml of ethanol. The solution was introduced into 30 ml of an aqueous solution containing 375 mg of Labrasol™ (Gattefosse) and 300 mg of Poloxamer 407™, and the whole mixture was stirred to obtain a homogenous solution. According to the procedure in Example 1, the orally administrable nanoparticle formulation containing ceftriaxone was prepared. According to the method of Example 1, the particle size and degree of dispersion were measured, and as s result, the mean particle size was 199.0 nm, and the degree of dispersion was 0.135.

Comparative Example 5

The liquid formulation was prepared according to the same method as Example 6, except using ceftriaxone instead of the complex of ceftriaxone and the counter-ion substance, and using neither polymer nor microfluidizer. According to the method of Example 1, the particle size and degree of dispersion were measured. As a result, the mean particle size was 149.4 nm, and the degree of dispersion was 0.124.

Example 7

Preparation of an Orally Administrable Nanoparticle Formulation Containing Ceftriaxone 240 mg of Ceftriaxone-counter-ion complex and 1200 mg of Capryol™ (Gattefosse) were dissolved in 15 ml of ethanol. The solution was introduced into 30 ml of an aqueous solution containing 240 mg of Labrasol™, 30 mg of chitosan and 300 mg of Poloxamer 407™, and the whole mixture was stirred. Then, according to the method of Example 1, the orally administrable nanoparticle formulation containing ceftriaxone was prepared. 300 mg of citric acid was added as an additive to increase the solubility of chitosan. According to the method of Example 1, the particle size and degree of dispersion were measured, and as a result, the mean particle size was 290.1 nm, and the degree of dispersion was 0.197.

Experiment 1

Measurement of Drug Entrapping Rate

500 μl of the liquid formulations prepared from the above Examples 1, and 1a to 7, and Comparative Examples 1 to 5 were dispersed into 500 μl of distilled water. Then, the dispersions were introduced into Centricon YM-30™ (fractionation MW: 30,000, Millipore), and centrifuged at the relative centrifuge force of 1500 g for 60 minutes. The drug was analyzed from the above separated filtrate, and the drug entrapping rate in the nanoparticle was calculated. The results are shown in the following Table 4.

TABLE 4

Drug entrapping rate in orally administrable nanoparticle formulations

| | Drug entrapping rate (%) |
|---|---|
| Example 1 | 99.8 |
| Example 1a | 95.7 |
| Example 2 | 98.7 |
| Example 3 | 97.2 |
| Example 4 | 90.3 |
| Example 5 | 91.3 |
| Example 6 | 90.5 |
| Example 7 | 92.0 |
| Comparative Example 1 | 72.4 |
| Comparative Example 2 | 64.8 |
| Comparative Example 3 | 70.7 |
| Comparative Example 4 | 92.6 |
| Comparative Example 5 | 40.8 |

Experiment 2

Evaluation of Enzyme Degradability

Degradation by Protease/Lipase, Pancreatin

Lipases are present in vivo, and nanoparticles composed of lipids should be stable against lipases such that insulin entrapped in lipid nanoparticles is not exposed to the exterior and so is not degraded by proteases. The formulations of examples and comparative examples were tested for their stability against in vivo enzyme degrading proteins and lipids, pancreatin.

5 ml of the liquid formulations prepared from the above Examples 1, 1a and 3 to 5, and Comparative Examples 1 to 4 were introduced into 15 ml of pH 7.4 buffer containing 0.0067% pancreatin (USP grade). The reaction was performed at 37° C. for 0, 1, 3 and 5 hours, and the residual amount of insulin was measured and shown in the following Table 5.

TABLE 5

Stability of orally administrable nanoparticle formulations containing insulin against pancreatin

| | Residual amount of insulin (%) | | | |
|---|---|---|---|---|
| | 0 hr | 1 hr | 3 hrs | 5 hrs |
| Example 1 | 100.0 | 95.8 | 93.6 | 91.6 |
| Example 1a | 100.0 | 100.0 | 97.5 | 93.5 |
| Example 3 | 100.0 | 100.0 | 97.5 | 93.5 |
| Example 4 | 100.0 | 99.1 | 96.8 | 93.4 |
| Example 5 | 100.0 | 92.7 | 92.0 | 91.3 |
| Comparative Example 1 | 100.0 | 9.1 | 0.8 | 0 |
| Comparative Example 2 | 100.0 | 87.5 | 82.6 | 82.1 |
| Comparative Example 3 | 100.0 | 91.6 | 69.2 | 57.2 |
| Comparative Example 4 | 100.0 | 51.2 | 14.9 | 14.5 |

As shown in the above Tables 4 and 5, Examples 1 to 5 formulations containing the insulin-counter-ion complex and the lipid/polymer had high drug entrapping rate and enzyme stability. By contrast, Comparative Example 1 formulation containing only lipid and Comparative Example 4 formulation containing only polymer had extremely low stability against enzyme, that is, the stability of insulin against pancreatin after 5 hours was just less than 20%.

In particular, Comparative Examples 1 & 2 nanoparticle formulations prepared from insulin, not from insulin-counter-ion complex, had low drug entrapping rate. Comparative Example 2 formulation containing polymer had higher stability against enzyme than Comparative Example 1 formulation containing no polymer, as shown in Table 5.

Comparative Example 3 formulation prepared by using only microfluidizer in preparing nanoparticle formulation had lower entrapping rate of insulin-counter-ion complex and lower stability against enzyme than Example 1 formulation prepared by first using such solubilizing agent as ethanol and then using microfluidizer. Example 1a nanoparticle formulation prepared by using solubilizing agent without using microfluidizer had high drug entrapping rate and stability against enzyme like Example 1 formulation.

As shown above, nanoparticle formulations prepared from insulin, not from an insulin-counter-ion complex, have low drug entrapping rate, and nanoparticle formulations composed of a lipid and a polymer have high stability against enzyme. Further, only the employment of microfluidizer is insufficient, and preliminary formation of nanoparticles with a solubilizing agent is necessary for obtaining nanoparticle formulations with high drug entrapping rate and stability against enzyme.

Consequently, the nanoparticles of the present invention prepared by forming a drug-counter-ion complex and entrapping the complex in a carrier composed of a lipid and a polymer were confirmed to have not only excellent drug entrapping rate but also excellent stability against lipases and proteases.

Experiment 3

Evaluation of Formulation from Example 1

Animal experiments were performed using the orally administrable nanoparticle liquid formulation prepared from Example 1.

(1) Diabetes Induction 45 mg/kg of streptozocin (Sigma) was intraperitoneally injected twice to normal male Sprague Dawley rats weighing about 180-220 g at the interval of two days to produce type I diabetic rats. After one week, the rats were fast for 12 hours, and then, the blood was gathered therefrom and their blood glucose was measured. As a result, the rats having the blood glucose of 300 mg/dl or more were considered type I diabetic rats, and used for the subsequent experiment. The blood glucose was measured using Glucotrand2™ (Roche).

(2) Measurement of Physiological Activity of Insulin in the Orally Administrable Nanoparticle Liquid Formulation 2 ml of the nanoparticle liquid formulation prepared from Example 1 was dispersed into 2 ml of physiological saline, and intramuscularly injected to type I diabetic rats at 3 IU/kg of insulin.

As reference group, insulin diluted in pH 7.4 buffer was intramuscularly injected to type I diabetic rats at 3 IU/kg of insulin. The blood was gathered from tail vein at given time interval.

Figure 2:
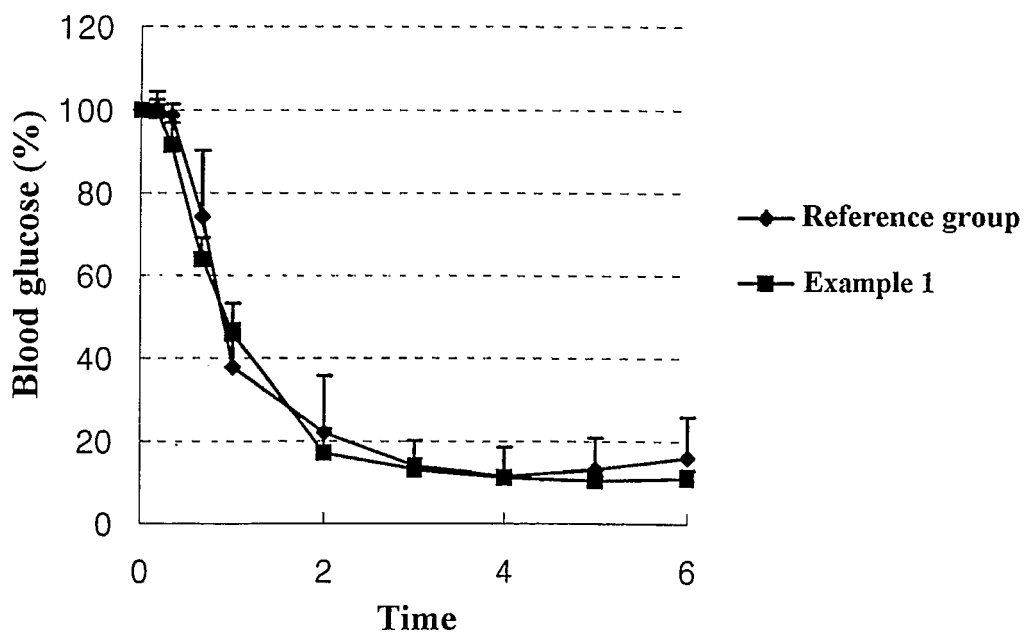

As shown in FIG. 2, comparing the physiological activities of insulin in the orally administrable nanoparticle liquid formulation of the present invention and the insulin solution, the nanoparticle liquid formulation of the present invention was confirmed to retain the physiological activity of insulin intact. Therefore, animal experiments were performed using the liquid formulation of the present invention, below.

(3) Gastrointestinal Absorption Test of the Orally Administrable Nanoparticle Liquid Formulation 1) Measurement of Blood Glucose Type I diabetic rat was ether-anesthetized, and the abdomen was opened. The small intestine was taken and the liquid formulation containing insulin was administered to 5 cm upper of the top of appendix at 20 IU/kg. Then, the incision was sutured, and the diabetic rat was allowed to move and drink water ad libitum.

For test groups, the formulations of Example 1, Comparative Example 1 and Example 1 a were used. The formulation of Comparative Example 1 was the nanoparticle formulation containing neither insulin-counter-ion complex nor polymer, and so having lower drug entrapping rate and enzyme stability, compared with that of Example 1. The formulation of Example 1a had high drug entrapping rate and enzyme stability, but was the nanoparticle formulation with larger particle size than that of Example 1 by not using the microfluidizer. As reference group 1, pH 7.4 of phosphate buffer containing insulin was administered at 20 IU/kg via the same route as Example 1, and as reference group 2, the insulin injectable solution was subcutaneously injected at 0.2 IU/kg.

Blood was gathered from tail vein at 0, 0.5, 1, 1.5, 2, 3, 5 and 7 hours after drug administration, and blood glucose was measured. Blood glucose values were measured on the basis of the initial value before administration as 100%.

Figure 3:
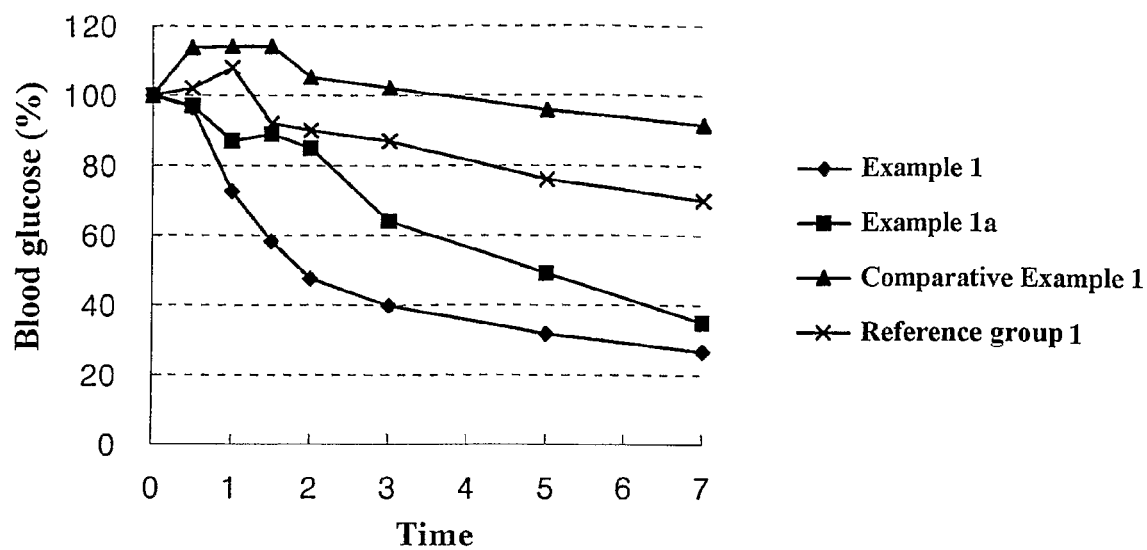
FIG. 3 is a graph showing the relative blood glucose concentration after intra-intestinally administering the oral nanoparticle composition of the present invention containing insulin as an active ingredient to type 1 diabetic rats in Experiment 3(3)1.
- ◆ -: Reference group 1 (insulin-containing buffer of pH 7.4, dosage of insulin 20 IU/kg)
- ■ -: Example 1 (dosage of insulin 20 IU/kg)
- ▲ -: Comparative Example 1 (dosage of insulin 20 IU/kg)
- X -: Example 1a (dosage of insulin 20 IU/kg)

As shown in FIG. 3, blood glucose was reduced by about 73% in case of administering the formulation of Example 1, but blood glucose was not nearly reduced in case of administering the formulation of Comparative Example 1. Further, the blood glucose reduced area of Example 1a formulation prepared by omitting passing through the microfluidizer was about 70% of that of Example 1.

As shown above, the nanoparticle formulation entrapping insulin, not insulin-counter-ion complex, only in lipid carrier did not nearly show blood glucose reducing activity in vivo. Also, blood glucose reducing activity could be enhanced by about 40% by reducing the particle size with passing through the microfluidizer during preparing the lipid nanoparticle formulation.

Figure 4:
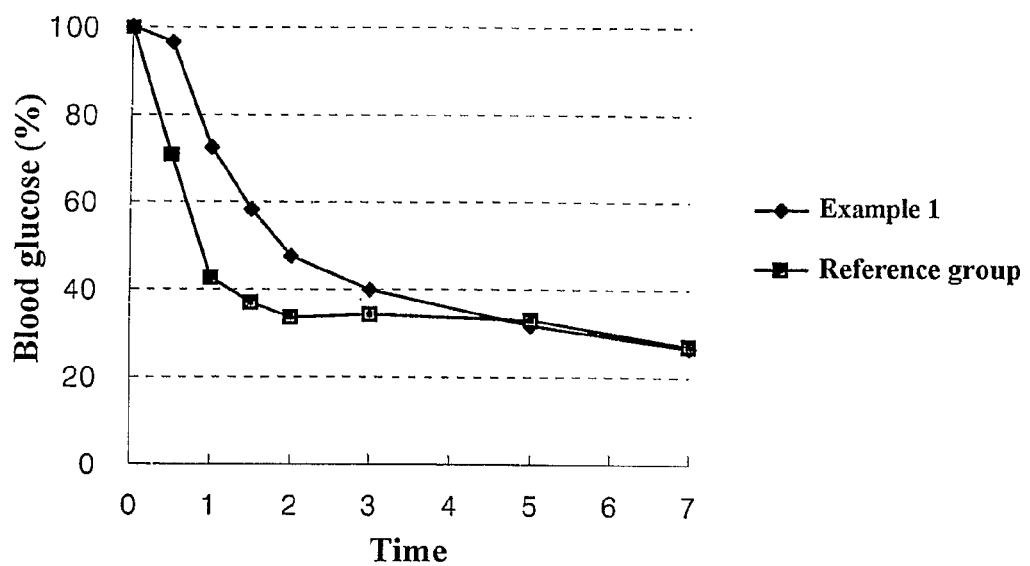
FIG. 4 is a graph showing the relative blood glucose concentration after intra-intestinally administering the oral nanoparticle composition of the present invention containing insulin as an active ingredient to type 1 diabetic rats in Experiment 3(3)1.
- ◆ -: Example 1 (dosage of insulin 20 IU/kg)
- ■ -: Reference group 2 (insulin injectable solution, subcutaneous injection, dosage of insulin 0.2 IU/kg)

As shown in FIG. 4, administration of Example 1 formulation showed very similar blood glucose reducing activity to subcutaneous injection of 0.2 IU/kg insulin.

2) Measurement of Blood Concentration of Insulin

Blood glucose was measured according to the above described method. For experiment, Example 1, Comparative Example 1 and Example 1a formulations were used, and for the control group, the orally administrable nanoparticle liquid formulation containing no insulin was administered via the same route as Example 1, and as the reference group, insulin injectable solution was subcutaneously injected at 0.2 IU/kg.

Blood was gathered from tail vein at 0, 0.5, 1, 1.5, 2, 3 and 5 hours after drug administration, and the blood concentration of insulin was measured using insulin analysis kit (Coat-a-count™, Diagnostic Products Corporation).

Figure 5:
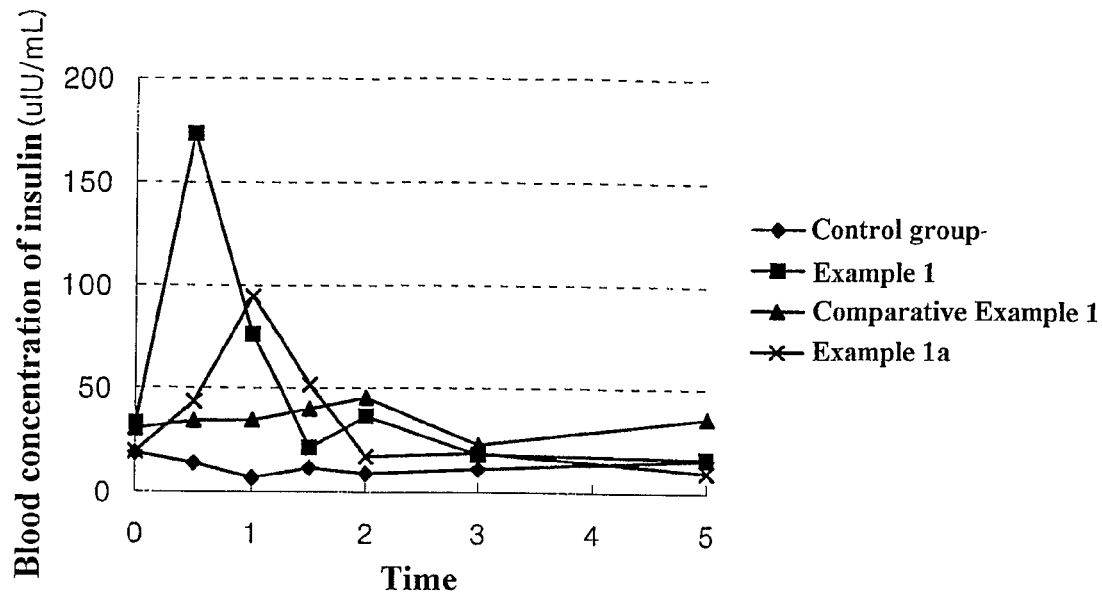
FIG. 5 is a graph showing the concentration of insulin after intra-intestinally administering the oral nanoparticle composition of the present invention containing insulin as an active ingredient to type I diabetic rats in Experiment $3(3)_2$).
- ◆ -: Control group (oral nanoparticle composition with no insulin)
- ■ -: Example 1 (dosage of insulin 20 IU/kg)
- ▲ -: Comparative Example 1 (dosage of insulin 20 IU/kg)
- X -: Example 1a (dosage of insulin 20 IU/kg)

As shown in FIG. 5, the blood concentration of insulin was less than 20 µIU/ml in the control group containing no insulin, but the maximal blood concentration was about 170 µIU/ml, and so insulin absorption rate was high, in Example 1 formulation. Comparative Example 1 formulation entrapping insulin, not insulin-counter-ion complex, in only lipid carrier showed only about 15 µIU/ml of insulin absorption rate at the time of maximal blood concentration. Example 1a formulation not passing through the microfluidizer showed about 70 µIU/ml of insulin absorption rate at the time of maximal blood concentration. In addition, comparing insulin increasing areas (AUC) according to time relative to the initial insulin concentration, Example 1 formulation showed increased AUC by about 140% compared with Example 1a formulation. This is similar to results of comparing blood concentration reducing areas according to time.

It was confirmed that entrapping insulin-counter-ion complex in a lipid carrier containing a polymer, and further, reducing the particle size by passing through a high pressure homogenizer are very effective to increase insulin absorption rate in type I diabetic rats.

Figure 6:
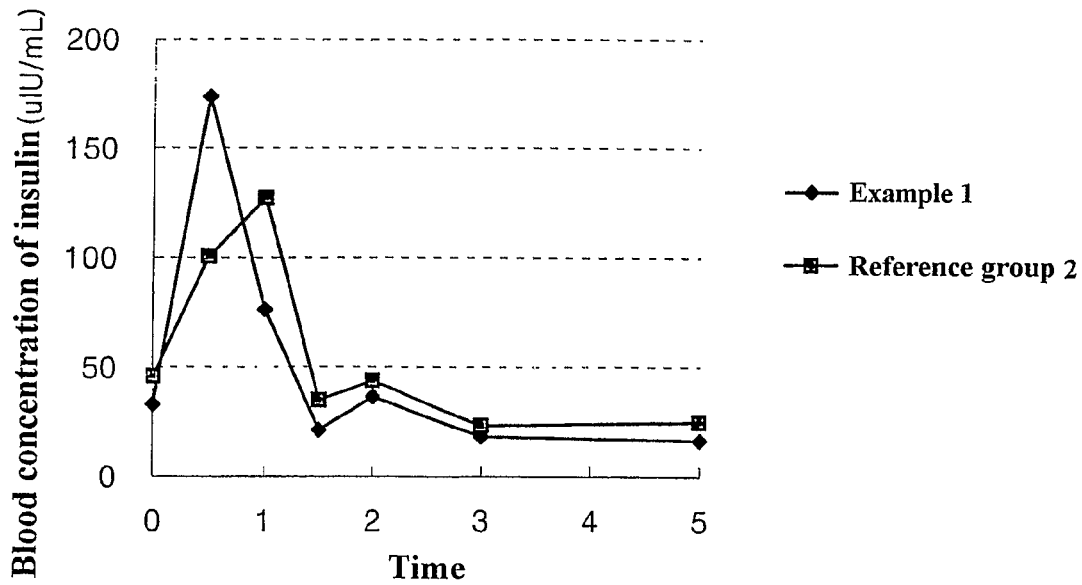
FIG. 6 is a graph showing the concentration of insulin after intra-intestinally administering the oral nanoparticle composition of the present invention containing insulin as an active ingredient to type I diabetic rats in Experiment $3(3)_2$).
- ◆ -: Example 1 (dosage of insulin 20 IU/kg)
- ■ -: Reference group (insulin injectable solution, subcutaneous injection, dosage of insulin 0.2 IU/kg)

As shown in FIG. 6, administration of Example 1 formulation showed the similar insulin blood concentration profile to subcutaneous injection of 0.2 IU/kg of insulin which is applied to early stage of diabetic patients.

Experiment 4

Evaluation of Formulations from Examples 6, 7 and Comparative Example 5

Animal experiments were performed using the orally administrable nanoparticle liquid formulation containing ceftriaxone prepared from Examples 6 and 7, and Comparative Example 5.

(1) Gastrointestinal Absorption Test of the Orally Administrable Nanoparticle Liquid Formulation 1) Measurement of Blood Glucose Normal rat (Sprague Dawley, male, weighing about 200 g) was ether-anesthetized, and the abdomen was opened. The duodenum was taken and the nanoparticle liquid formulation containing ceftriaxone was administered thereto at 40 mg/kg as ceftriaxone.

The formulations of Examples 6 and Example 7, and Comparative Example 5 were used for test groups. The formulation of Comparative Example 5 is one containing neither ceftriaxone-counter-ion complex nor polymer, and so having lower drug entrapping rate and incapable of controlling drug dissolution compared with that of Example 6.

Blood was gathered from tail vein at 0, 0.5, 1, 1.5, 2, 3 and 4 hours after the drug administration, and analyzed according to ceftriaxone analysis method of the US Pharmacopoeia. The blood was centrifuged at 3000 rpm for 10 minutes, and pretreated by adding the equal amount of acetonitrile thereto.

As reference group 1, ceftriaxone dissolved in water was administered at 40 mg/kg via the same route as Example 6.

As reference group 2, ceftriaxone dissolved in a physiological saline was intravenously injected at 20 mg/kg.

Figure 7:
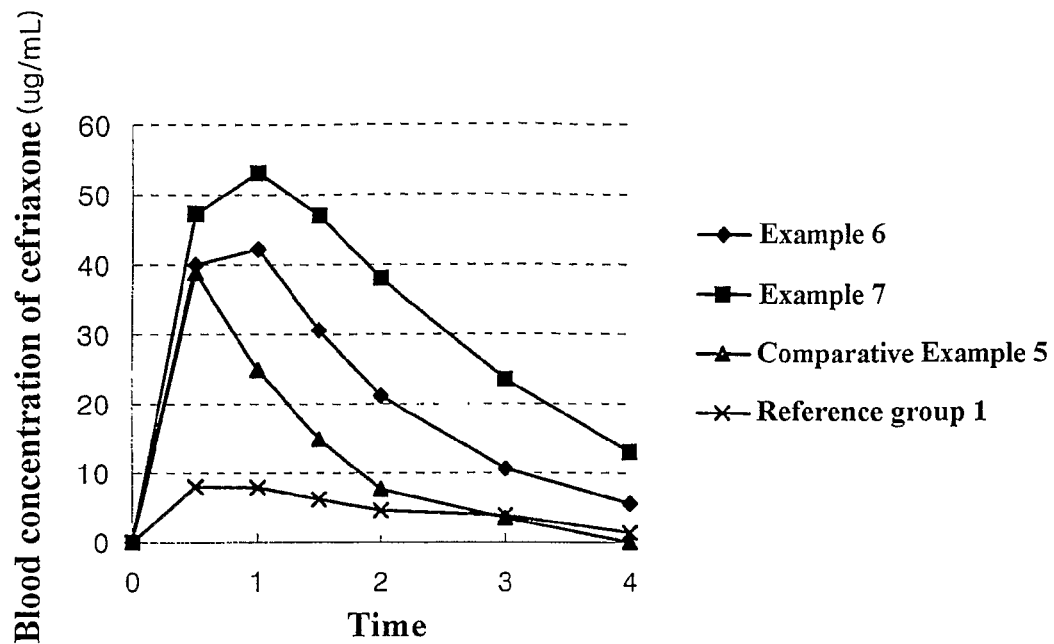
FIG. 7 is a graph showing the concentration of ceftriaxone after intra-duodenally administering the oral nanoparticle composition of the present invention containing ceftriaxone as an active ingredient to normal rats in Experiment 4(1)1.
- ◆ -: Example 6 (dosage of ceftriaxone 40 mg/kg)
- ■ -: Example 7 (dosage of ceftriaxone 40 mg/kg)
- ▲ -: Comparative Example 5 (dosage of ceftriaxone 40 mg/kg)
- X -: Reference group 1 (ceftriaxone containing aqueous solution, dosage of ceftriaxone 40 mg/kg)
Figure 8:
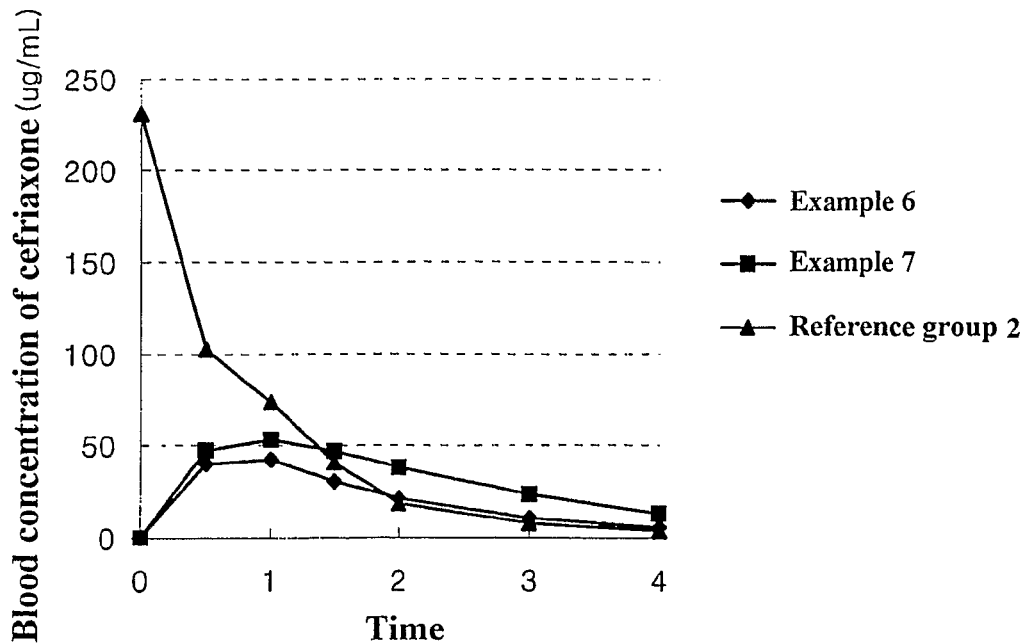
FIG. 8 is a graph showing the concentration of ceftriaxone after intra-duodenally administering the oral nanoparticle composition of the present invention containing ceftriaxone as an active ingredient to normal rats in Experiment 4(1)1.
- ◆ -: Example 6 (dosage of ceftriaxone 40 mg/kg)
- ■ -: Example 7 (dosage of ceftriaxone 40 mg/kg)
- ▲ -: Reference group 2 (ceftriaxone injectable solution, intravenous injection, dosage of ceftriaxone 20 mg/kg)

As shown in FIGS. 7 and 8, bioavailability was 22.8% and 35.1% in case of administering the formulations of Examples 6 and 7, respectively, compared with the intravenous injection. By contrast, ceftriaxone was not nearly absorbed in vivo in reference group 1 to which the aqueous solution of ceftriaxone was administered, and the maximal blood concentration was lower and bioavailability was merely about 12.4% in the group to which the formulation of Comparative Example 5 was administered wherein ceftriaxone was entrapped only in lipid, compared with the groups to which that the formulations of the examples were administered. In case of administering the formulations of Examples 6 and 7, the blood concentration of ceftriaxone was decreased more slowly than administering the formulation of Comparative Example 5. Particularly, the blood concentration of drug was maintained higher after 1.5 hours while the initial drug concentration was lower than reference group 2 to which ceftriaxone was intravenously injected. From this result, it was considered that the composition of the present invention can reduce side effects from the high initial blood concentration and exhibit the pharmacological effect for longer period of time than the injectable solution.

As shown above, the composition of the present invention has high entrapping rate of a water-soluble drug in nanoparticles, protects the drug from lipases or proteases in vivo, and has high absorption rate in the gastrointestinal tract, and therefore, shows high blood concentration of drug.

INDUSTRIAL APPLICABILITY

As described above, the orally administrable nanoparticle composition of the present invention has high entrapping rate of a water-soluble drug in the nanoparticle, and protects the unstable drug from gastrointestinal enzymes, and has high absorption rate to the gastrointestinal membrane. Therefore, it is extremely useful as drug delivery system for enhancing the bioavailability of water-soluble drugs whose oral administration has been limited due to charges thereof.

What is claimed is:

1. An orally administrable composition containing particles with a particle size of 500 nm or less, comprising:
    0.1 to 30 weight % of a complex of a charged water-soluble drug and a counter-ion substance in which the charged water-soluble drug is ionically bonded with the counter-ion substance, wherein said counter-ion substance is an anionic compound selected from the group consisting of sodium salt of $C_{8-18}$ fatty acid, sodium salt of bile acid, sodium alginate, and sodium carboxymethylcellulose, or a cationic compound selected from the group consisting of carnitine salt, benzalkonium chloride, cetrimide, and mixtures thereof;
    0.5 to 80 weight % of a lipid, wherein said lipid is an aliphatic alcohol selected from the group consisting of monoglyceride, diglyceride, propyleneglycol fatty acid ester, glycerol fatty acid ester, cetostearyl alcohol, cetyl alcohol, and mixtures thereof;
    0.5 to 80 weight % of a polymer, wherein said polymer is selected from the group consisting of methacrylic acid copolymer, hydroxypropyl methylcellulose phthalate, hydroxypropyl methylcellulose acetate succinate, cellulose acetate phthalate, shellac, chitosan, hydroxypropyl methylcellulose and its derivative, ethylcellulose, methylcellulose, polyvinylalcohol, sodium alginate, carbomer, and mixtures thereof;
    0.1 to 30 weight % of a cryoprotective agent, wherein the cryoprotective agent is selected from the group consisting of glucose, mannitol, sorbitol, trehalose, amino acid, albumin, and mixtures thereof; and
    1 to 80 weight % of an emulsifier,
    wherein the weight ratio of said lipid and said polymer is in the range of 1:0.05 to 3 and said complex is entrapped in said lipid and said polymer is inserted between said lipid.

2. The composition of claim 1, wherein 70% or more of the water-soluble drug is entrapped in the particles.

3. The composition of claim 1, wherein 80% or more of the charged water-soluble drug is retained in the particles when the composition is mixed with pancreatin.

4. The composition of claim 1, wherein the charged water-soluble drug is a protein/peptide drug selected from the group consisting of insulin, erythropoietin, calcitonin, growth hormone, interferon, and somatostatin.

5. The composition of claim 1, wherein the charged water-soluble drug is one charged in water selected from the group consisting of heparin, cepha antibiotic, sodium alendronate, sodium etidronate, and sodium pamidronate.

6. The composition of claim 1, wherein the sodium salt of fatty acid is selected from the group consisting of sodium docusate, sodium oleate, sodium lauryl sulfate, sodium caproate, and sodium laurate.

7. The composition of claim 1, wherein the molar ratio of the water-soluble drug and the counter-ion substance is in the range of 1:0.1 to 20.

8. The composition of claim 7, wherein the molar ratio of the charged water-soluble drug and the counter-ion substance is in the range of 1:3 to 10.

9. The composition of claim 1, wherein the weight ratio of the lipid and the polymer is in the range of 1:0.2 to 1.

10. The composition of claim 1, wherein the emulsifier is selected from the group consisting of polyoxyethylene polyoxypropylene copolymer, polyethyleneglycol alkyl ether, polyoxyethylene castor oil, polyoxyethylene sorbitan fatty acid ester, transesterification product of natural vegetable oil triglyceride and polyalkylene polyol, glycerol fatty acid ester, vitamin E polyethyleneglycol succinate, lecithin, sodium lauryl sulfate, bile acid and its derivative, and mixtures thereof.

11. The composition of claim 1, further comprising 50 weight % or less of a solubilizing agent.

12. The composition of claim 11, wherein the solubilizing agent is selected from the group consisting of $C_{1-8}$ alcohol, dimethylsulfoxide, dichloromethane, toluene, propyleneglycol, polyethyleneglycol, and 12-hydroxystearate.

13. The composition of claim 1, wherein the particle size of the particles is in the range of 20 to 300 nm.

14. A method for preparing the orally administrable nanoparticle composition of claim 1, comprising the steps of:
    (a) ionically bonding a charged water-soluble drug with a counter-ion substance to form a complex of the water-soluble drug and the counter-ion substance, wherein said counter-ion substance is an anionic compound selected from the group consisting of sodium salt of $C_{8-18}$ fatty acid, sodium salt of bile acid, sodium alginate, and sodium carboxymethylcellulose, or a cationic compound selected from the group consisting of carnitine salt, benzalkonium chloride and cetrimide;
    (b1) adding a lipid, a polymer and a solubilizing agent to the complex obtained from step (a) and dissolving them, and adding the obtained solution to an aqueous solution containing an emulsifier, to obtain a homogeneous liquid phase, or
    (b2) adding a lipid and a solubilizing agent to the obtained complex and dissolving them, and adding the obtained solution to an aqueous solution containing a polymer and an emulsifier, to obtain a homogeneous liquid phase; and
    (c) eliminating the solubilizing agent from the mixture obtained from step (b1) or (b2).

15. The method of claim 14, further comprising step (d) of minimizing the particle size using a microfluidizer.

16. The method of claim 14, wherein the charged water-soluble drug is obtained by treating the water-soluble drug with a pH adjusting agent to confer charge thereon in step (a).

17. The method of claim 16, wherein the pH adjusting agent is selected from the group consisting of hydrochloric acid, phosphoric acid, carbonic acid, citric acid, sodium hydroxide, sodium/potassium monohydrogen phosphate, sodium/potassium dihydrogen phosphate, sodium phosphate, sodium citrate, and mixtures thereof.

* * * * *